United States Patent
Atthoff et al.

(10) Patent No.: US 9,028,466 B2
(45) Date of Patent: May 12, 2015

(54) ADAPTER FOR USE IN CONNECTING TO A FIRST PERCUTANEOUS INTRODUCER

(75) Inventors: Björn Atthoff, Uppsala (SE); Fredrik Preinitz, Uppsala (SE)

(73) Assignee: St. Jude Medical Coordination Center BVBA, Zaventem (BE)

( * ) Notice: Subject to any disclaimer, the term of this patent is extended or adjusted under 35 U.S.C. 154(b) by 1034 days.

(21) Appl. No.: 12/480,318

(22) Filed: Jun. 8, 2009

(65) Prior Publication Data

US 2010/0312224 A1    Dec. 9, 2010

(51) Int. Cl.
*A61M 25/16*    (2006.01)
*A61M 39/10*    (2006.01)
*A61M 39/02*    (2006.01)

(52) U.S. Cl.
CPC ....... *A61M 39/1011* (2013.01); *A61M 39/0247* (2013.01)

(58) Field of Classification Search
CPC .............. A61M 39/12; A61M 2039/1066; A61M 2039/1077; A61M 39/14; A61M 39/10; A61M 39/1011; A61M 39/0247
USPC .................. 604/533–535, 536–539
See application file for complete search history.

(56) References Cited

U.S. PATENT DOCUMENTS

| | | | | |
|---|---|---|---|---|
| 2,874,981 A * | 2/1959 | Sherwood | ...................... | 285/238 |
| 3,235,133 A | 2/1966 | Zimmerman et al. | | |
| 3,685,795 A * | 8/1972 | Caster | .......................... | 251/342 |
| 4,056,116 A * | 11/1977 | Carter et al. | .................. | 137/68.3 |
| 4,080,965 A * | 3/1978 | Phillips | ......................... | 604/411 |
| 4,634,432 A * | 1/1987 | Kocak | ..................... | 604/167.04 |
| 4,676,782 A | 6/1987 | Yamamoto et al. | | |
| 4,744,364 A | 5/1988 | Kensey | | |
| 4,772,276 A * | 9/1988 | Wiita et al. | ................... | 604/533 |
| 5,021,059 A | 6/1991 | Kensey et al. | | |
| 5,061,274 A * | 10/1991 | Kensey | ......................... | 606/213 |
| 5,147,336 A | 9/1992 | Wendell et al. | | |
| 5,507,535 A * | 4/1996 | McKamey et al. | ........ | 285/149.1 |
| 5,776,117 A * | 7/1998 | Haselhorst et al. | ........... | 604/533 |
| 2002/0173820 A1 | 11/2002 | Akerfeldt et al. | | |
| 2004/0204741 A1 | 10/2004 | Egnelov et al. | | |
| 2005/0245899 A1* | 11/2005 | Swisher | ....................... | 604/533 |
| 2006/0135991 A1* | 6/2006 | Kawaura et al. | ............. | 606/213 |
| 2006/0173420 A1* | 8/2006 | Fangrow, Jr. | .................. | 604/247 |
| 2006/0173492 A1 | 8/2006 | Akerfeldt et al. | | |
| 2006/0271012 A1* | 11/2006 | Canaud et al. | ................. | 604/500 |
| 2008/0262475 A1 | 10/2008 | Preinitz | | |
| 2009/0299337 A1 | 12/2009 | Groppi et al. | | |

FOREIGN PATENT DOCUMENTS

| | | |
|---|---|---|
| EP | 1479405 A1 | 11/2004 |
| EP | 1 305 076 B1 | 12/2004 |
| GB | 8229 A | 0/1894 |
| WO | WO 00/56620 A1 | 9/2000 |
| WO | WO 2007/060218 A1 | 5/2007 |

OTHER PUBLICATIONS

US 5,766,117, 06/1998, Haselhorst et al. (withdrawn)

* cited by examiner

*Primary Examiner* — Edelmira Bosques
(74) *Attorney, Agent, or Firm* — Foley & Lardner LLP

(57) ABSTRACT

A universal introducer adapter which can be inserted into a pre-placed introducer of arbitrary dimensions eliminates the need to replace or remove the introducer. The adapter includes a distal portion with a retainer in the form of a soft elastic material.

40 Claims, 3 Drawing Sheets

ADAPTER FOR USE IN CONNECTING TO A FIRST PERCUTANEOUS INTRODUCER

FIELD OF THE INVENTION

The present invention relates generally to an introducer adapter for an introducer, which through a percutaneous puncture is used to obtain access to blood vessels, cavities, or other bodily tissues or organs in order to perform a medical procedure, and more particularly to an introducer adapter being provided with an elongated distal end portion, which further comprises a soft gasket material or packing material, by which the introducer adapter can be attached to an introducer already in place at the percutaneous puncture site.

BACKGROUND OF THE INVENTION

An introducer is an elongated tubular member, which in the medical field is used to gain access to a particular site within a patient's body. It should be noted that herein the term "introducer" is, unless otherwise indicated, used as indicative of an introducer sheath, which comprises at least one proximal entry port. Depending on the medical procedure, the design of an introducer can vary. For example, the proximal end can comprise attachment means, usually referred to as "hubs," for a medical instrument. Additionally, an entry port can comprise sealing material to prevent leakage of, for example, bodily fluids; and an introducer can comprise several entry ports. Further, different introducer manufacturers have different designs for their introducers.

Usually the medical procedure wherein an introducer is used commences with a puncture operation, in which a hollow needle is introduced at a point on a patient's skin, and is then advanced through tissues beneath the skin to the desired position in the organ of interest, e.g. a blood vessel. Typically a guide wire is then introduced through the needle, whereupon the needle is removed, leaving only the guide wire in place. Then an introducer, usually together with a dilator, is advanced over the guide wire. After removal of the guide wire and dilator, access to the organ has now been obtained through the lumen of the tubular introducer sheath.

The procedure described above can be used to gain access to a blood vessel for performing different types of intravascular operations. When the operation in question is completed, the puncture hole in the blood vessel can be sealed by means of a closure device, wherein an inner member of said closure device is positioned at an inner surface of the vessel wall by means of an insertion instrument and which is held in place by a suture or filament. The suture or filament extends from the closure device, through tissue overlying the vessel, and out of the skin surface. An example of this sealing technique is disclosed in U.S. Pat. No. 4,744,364. Another method, wherein an anchor is placed at an inner surface of a vessel wall and a sealing member is placed at an outer surface of the vessel wall, is disclosed in U.S. Pat. No. 5,021,059. These publications are hereby incorporated by reference for the devices and methods described therein.

In many cases several different medical procedures need to be performed on a patient using the same access site, e.g. a percutaneous blood vessel puncture. Some examples of different procedures involving such a percutaneous puncture are insertion of and measurements using a sensor guide wire, placing a stent, performing angioplasty, and, in most cases, sealing the puncture, as described above. Especially in the case of sealing a puncture, which follows subsequently to one or several different medical procedures, a need arises to switch introducer sheaths, due to specific requirements on, for example, the access path of the closure device in question.

SUMMARY OF THE INVENTION

As mentioned above, introducers are of many different designs and dimensions. Although the introducers known in the prior art serve their intended purposes, replacing one introducer by another introducer increases the risk of causing infection, excessive bleeding due to ruptures of blood vessels, and discomfort or pain to the patient. Prior art shows several examples of adapters, which are designed to be able to connect to an introducer. Two such examples of adapters are disclosed in European Patent No. 1305076 and U.S. Pat. No. 5,147,336, respectively. However, these adapters require a specific shape or dimension of a matching mating member on the introducer, and can consequently not be called universal introducer adapters. From prior art, it is further known to provide a connecting device for a tubular device, such as an introducer sheath, by providing an adapter with a tapered shape. One such example is disclosed in U.S. Pat. No. 5,776,117, which describes an adapter for connection to various-sized tubes, adapters and/or y-ports provided with several sections with different external diameters, together forming a roughly tapered shape, with a stepwise changing diameter. In addition, the adapter described in the U.S. Pat. No. 5,776,117 preferably requires an elastic tube, and is not truly universal in the sense of being able to connect to almost any commonly used dimension or type of tube. To be truly universal, an adapter needs to be able to connect and attach to all possible dimensions, or at least to all dimensions commonly used, of tubes or introducers. In an attempt to overcome these deficiencies, in the published U.S. Patent Application No. 2008/0262475, which is assigned to the present assignee, there is presented an introducer adapter comprising a tapered and threaded distal portion which is adapted to be screwed directly into the comparatively soft material of the inner wall of a pre-placed introducer. The entire contents of the '475 publication are incorporated herein by reference for the devices and methods discussed therein. Lately, introducers having a proximal end portion comprising a sleeve made from a comparatively hard material, such as stainless steel, have, however, been introduced on the market, thereby rendering an introducer adapter comprising a threaded distal portion less suitable for connection to these types of introducers.

Therefore there is still a need for a way to utilize an introducer, which is already in place in, for example, a blood vessel for a subsequent medical procedure, irrespective of the shape and dimensions of the pre-placed introducer.

An object of the present invention is to provide a universal introducer adapter which can be inserted into a pre-placed introducer of practically arbitrary dimensions, thereby eliminating the need to replace the introducer. A further object of some embodiments of the invention is to provide an introducer adapter which can be used to connect practically any pre-placed first introducer with practically any new second introducer, without having to remove the first introducer. Yet another object of some embodiments of the invention is to provide an introducer adapter comprising an insertion tool for a closure device.

According to one embodiment of the present invention, a universal adapter comprises an elongated distal portion provided with a soft material in the form of a gasket material or packing material, which functions as a retainer. In use, the elongated distal portion, with the soft retainer arranged thereupon, is introduced a certain distance into a proximal end portion of a pre-placed introducer. Due to the design and arrangement of the soft retainer and the distal portion as well as due to the pushing force applied, this manoeuvre causes initial stretching and thereby diameter-reduction of the material in the soft retainer, such that a portion of the soft retainer can be forced a certain distance into the proximal end portion of the pre-placed introducer. As will be more thoroughly explained below, subsequent retraction and removal of the introducer adapter is prevented by the deformation which, if such a movement is initiated, is then created in the material of the soft retainer. The effect of the procedure described above is that it is fairly easy to insert and attach the introducer adapter to the proximal end of an introducer, which is already in place in a puncture hole in, for example, a patient's femoral artery, but motion in the opposite direction, i.e. out of the pre-existing introducer, is prevented by deformation of the soft retainer material, which creates a bulge, which, in turn, restricts or prevents movement of the introducer adapter in the proximal direction, as will be more thoroughly described below.

To work properly as a retainer, a gasket material or packing material should according to the present invention have a preferred minimal length, such that enough deformation, i.e. a large enough bulge, can be created. The terms "gasket material" or "packing material" could in this respect be somewhat misleading, as the primary function of such a gasket material or packing material is not to act as a seal between the pre-placed introducer and the introducer adapter. A "true" seal, such as an O-ring, is typically rather short in the longitudinal direction, and would normally not provide an attachment that is stiff and reliable enough to properly function as a retainer for a second instrument, e.g. an introducer, in accordance with the present invention. The gasket material or packing material should further be soft enough and/or have a modulus of elasticity (Young's modulus) that is small enough to allow deformation, as will be detailed below.

To enhance the effect of the soft retainer deformation, the present invention comprises embodiments wherein such a retainer can be shaped into various forms, including a bulging shape, which is thickest in its middle portion and becomes thinner at its ends, and a saw-tooth shaped provided with a number of protrusions.

To even further improve the functioning of the introducer adapter, also the distal portion of the introducer adapter can be provided with different shapes. According to one embodiment of the present invention, the distal portion of the introducer adapter is provided with a barb-like shape, which has the dual capacity of both holding a soft retainer in place and improve the gripping of the adapter in a pre-existing introducer. In another embodiment, the distal portion of the introducer adapter narrows slightly in the proximal direction, something which has shown to provide a secure attachment to a pre-placed introducer.

DETAILED DESCRIPTION OF PREFERRED EMBODIMENTS

The present invention will be described in the context of a percutaneous puncture made to gain access to a blood vessel. However, it is within the scope of the present invention to use the invention in other medical procedures, such as obtaining access to the abdominal cavity or a specific organ through an introducer.

Figure 1A:
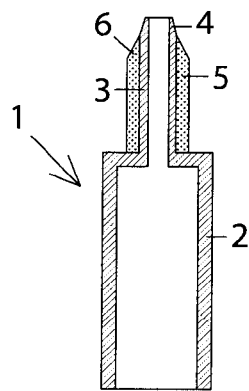
FIGS. 1a, 1b, and 1c illustrate schematically certain general principles of the present invention in accordance with a first embodiment of the introducer adapter.
Figure 1C:
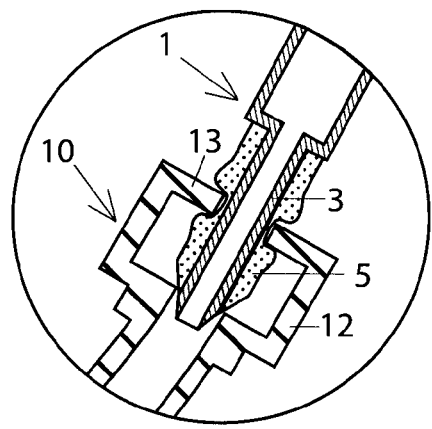
Figure 1B:
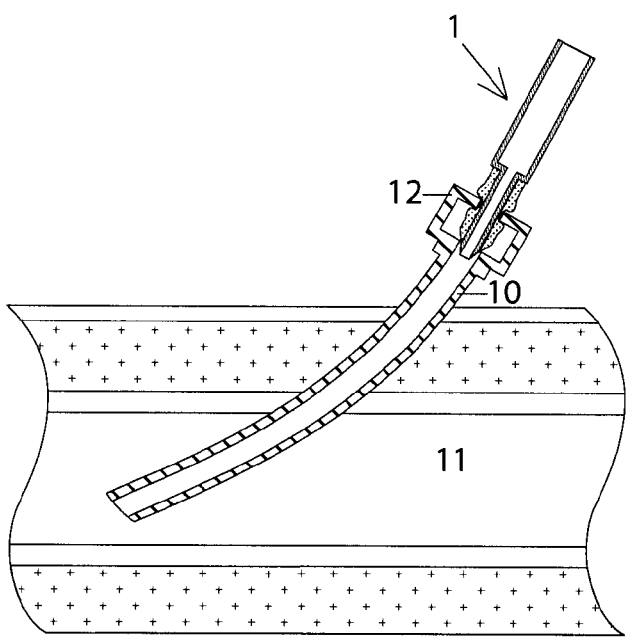

A first embodiment of an introducer adapter according to the present invention is schematically illustrated in FIG. 1a, and is, together with a pre-placed introducer, schematically illustrated in FIG. 1b, with an accompanying enlarged section shown in FIG. 1c. More specifically, FIG. 1a shows a cross-section of a portion of an introducer adapter 1 having a cylindrical mantle wall 2 with a first diameter. The introducer adapter 1 has further been provided with an elongated distal portion 3 having a second diameter, which preferably is smaller than the first diameter, and a preferably somewhat tapered distal end 4. In this embodiment, the length of elongated distal portion 3 is greater than the second diameter such as at least 1.5 times the second diameter, or at least 2 times the second diameter, or at least 3 times the second diameter. Around the distal portion 3, a retainer 5 formed of elastic material such as gasket material or packing material has been arranged. In this embodiment, the retainer 5 is placed over distal portion 3, which serves as an inner core. In this embodiment, the retainer 5 has been provided with a tapered distal end 6, but has otherwise a tubular shape. The retainer 5 can be held in place on the distal portion 3 by friction alone, but can otherwise be attached by, for example, glue. As will be appreciated from the description below, it can be advantageous to only attach the very distal end portion of retainer 5, because the more proximal portion of retainer 5 is then free to move a short distance and can thereby more easily deform. The last feature is applicable to all embodiments shown herein.

In this embodiment, the length of the retainer 5 is greater than an inner diameter of the retainer 5, such as the length being at least 1.5 times as great, or at least 2 times as great, or at least 3 times as great. In this embodiment, the wall thickness of the retainer 5 is at least 0.5 mm, such as at least 1.0 mm, such as at least 2.0 mm.

In use, the introducer adapter 1 is pushed into a proximal portion of an introducer, which already is in place in, for example, a patient's artery. This situation is schematically illustrated in FIG. 1b, where the introducer adapter 1 has been attached to a proximal portion (also referred to as a hub 12) of an introducer 10, whose distal portion, in a previous medical procedure, has been positioned in a vessel 11, such that the proximal portion is accessible at the outside of the patient's skin. More specifically, and as is more clearly seen in FIG. 1c, the distal portion 3 of the introducer adapter 1 has been pushed a distance into a hub 12, which constitutes the proximal end portion of introducer 10. In this position, the retainer 5 has been deformed by being compressed by contact with a proximal end rim 13 of the hub 12. Due to this deformation, any movement in the opposite direction, i.e. proximally or backwards out from the hub 12, is prevented, and the introducer adapter 1 is securely attached to the pre-placed introducer 10. If at least the proximal portion of the retainer 5 is free to move, i.e. is not attached to the distal portion 3 of the introducer adapter 1, it can be appreciated that the retainer 5 during the introduction thereof stretches out more easily, but is subsequently deformed and squeezed and stuck in the proximal end rim 13, to thereby prevent movement in the opposite direction.

In this embodiment, although the primary function of retainer 5 is to retain the adapter securely to introducer 10, retainer 5 also fills void(s) between adapter 1 and introducer 10 and thus provides a fluid tight seal between adapter 1 and introducer 10.

Figure 2:
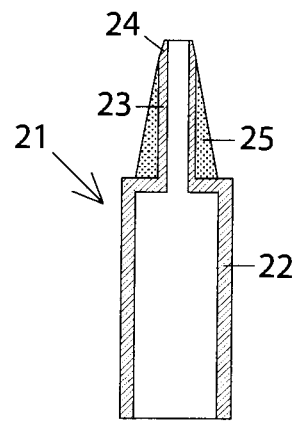
FIG. 2 illustrates schematically a second embodiment of a soft retainer which is part of an introducer adapter.

FIG. 2 illustrates a second embodiment of an introducer adapter 21 according to the present invention, wherein the introducer adapter 21 comprises a cylindrical mantle wall 22 having a first diameter and an elongated distal portion 23 having a second diameter, which preferably is smaller than the first diameter, and a preferably slightly tapered distal end 24. The introducer adapter 21 comprises further a retainer in the form of an elongated and hollow retainer 25, which is arranged around the elongated distal portion 23. In this embodiment, the retainer 25 has the shape of a truncated cone.

Figure 3:
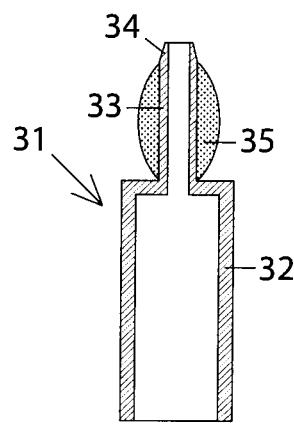
FIG. 3 illustrates schematically a third embodiment of a soft retainer which is part of an introducer adapter.

A third embodiment of an introducer adapter 31 is depicted in FIG. 3. The introducer adapter 31 has, like the introducer adapters described in conjunction with FIGS. 1a-c and FIG. 2, respectively, a cylindrical mantle wall 32 with a first diameter, and an elongated distal portion 33, with a second diameter and a preferably slightly tapered distal end 34. The introducer adapter 31 comprises further a retainer in the form of an elongated and hollow retainer 35, which is arranged around the elongated distal portion 33. In this embodiment, the retainer 35 has been given a bulging structure, with a diameter that is largest in the middle portion and narrows towards the proximal and distal ends.

Figure 4:
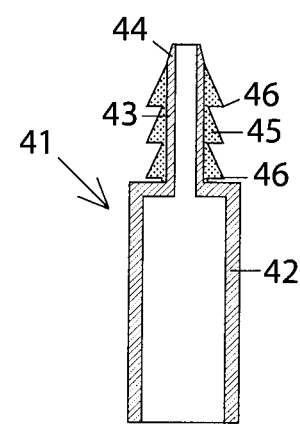
FIG. 4 illustrates schematically a fourth embodiment of a soft retainer which is part of an introducer adapter.

FIG. 4 shows a fourth embodiment of an introducer adapter 41, which has a cylindrical mantle wall 42 with a first diameter, and an elongated distal portion 43, with a second diameter and a preferably slightly tapered distal end 44. The introducer adapter 41 comprises further a retainer in the form of an elongated and hollow retainer 45, which is arranged around the elongated distal portion 43. In this embodiment, the retainer 45 has been given a saw-tooth shape, with a number of protrusions 46, which, like saw-teeth, radially extend further out from an imaginary longitudinal centreline at their proximal ends than at their distal ends.

Figure 5:
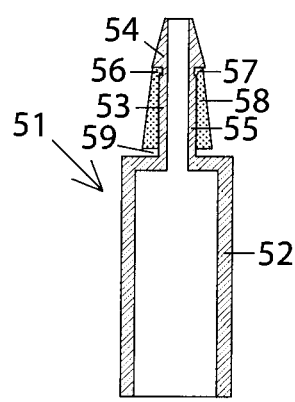
FIG. 5 shows the shape of the distal portion of a fifth embodiment of an introducer adapter.

A fifth embodiment of an introducer adapter 51 is illustrated in FIG. 5. In this embodiment, the introducer adapter 51 comprises a mantle wall 52 with a first diameter, and an elongated distal insertion portion 53, with a second diameter and whose most distal end is in the general form of a truncated cone, with a base portion 54 being somewhat larger, in the radial direction, than a more proximal portion 55 of the insertion portion 53. Thus, the insertion portion can be characterized as a proximal stem 55 provided with a distal head 54 having the shape of a frustum of a cone. Adjoining to the base of the truncated cone a small circumferential notch 56 has been provided. The notch facilitates attachment of a retainer in the form of a retainer 58, which is provided with a lug 57 that matches and extends into the notch 56. An arrangement comprising a notch in the insertion portion and a matching lug on the retainer could also be reversed, i.e. a lug on the insertion portion and a notch in the retainer. All embodiments presented herein could be provided with similar arrangements. The retainer 58 has otherwise the shape of a truncated cone, similar to the retainer 25 of FIG. 2, but—unlike the retainer 25 of FIG. 2—the retainer 58 ends a short distance distally of the proximal end of the insertion portion 53, such that a small gap 59 is provided between the distal end of the mantle wall 52 and the retainer 58. During insertion of the introducer adapter 51 into a pre-placed introducer, this gap 59 promotes stretching of the retainer 58. All embodiments presented herein could be provided with a similar gap.

Figure 6:
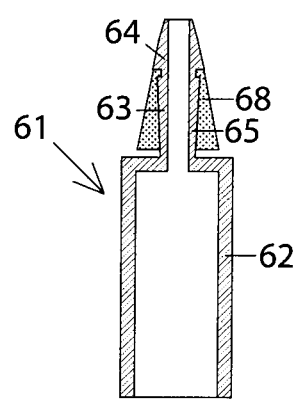
FIG. 6 shows the shape of the distal portion of a sixth embodiment of an introducer adapter.

FIG. 6 depicts a sixth embodiment of an introducer adapter 61, which is very similar to the introducer adapter 51 of FIG. 5, with an elongated distal insertion portion 63 comprising a stem 65 and head 64 having the shape of a truncated cone. In this sixth embodiment, however, the stem 65 widens slightly in a distal direction; and a retainer 68 has been given a matching shape.

As has been explained above, a very important application for the present invention is to provide a means for closing a percutaneous puncture without the need of changing introducers. To accomplish this purpose, an introducer adapter according to an embodiment of the present invention can be a more or less integrated part of an insertion tool for a closure device. Herein, the expression "more or less" is intended to imply that such an integration ranges from an instrument wherein an insertion tool and an introducer adapter actually are formed (e.g. moulded) in one piece to an instrument wherein an introducer adapter is loosely and/or releasably attached (e.g. by screwing or clamping) to a separate insertion tool.

Figure 7:
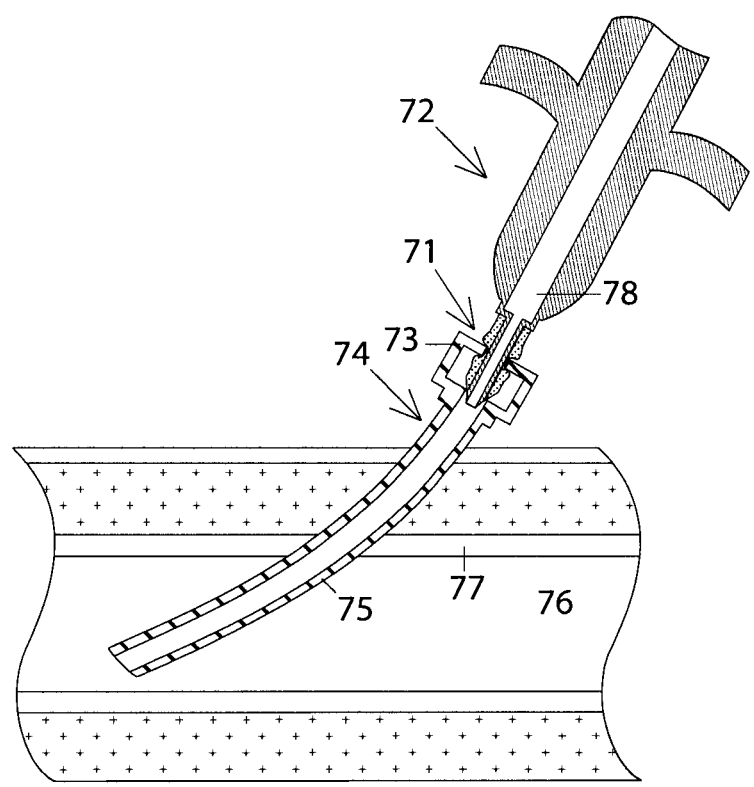
FIG. 7 illustrates how one introducer adapter according to the invention can be an integrated part of an insertion instrument for a closure device.

Such an embodiment of the present invention is schematically illustrated in FIG. 7, wherein an introducer adapter 71 constitutes the distal part of an insertion tool 72. As can be seen in the figure, the insertion tool 72 is by the introducer adapter 71 attached to a hub 73, which constitutes the proximal end portion of an introducer sheath 74, whose distal end 75 has been introduced into a vessel 76. Typically, the introducer has been utilized in a previous medical operation, which has left a puncture hole in a vessel wall 77, which now is going to be sealed or closed by a closure device (not shown) accommodated in the interior 78 of the insertion tool 72. Any of the introducer adapters shown in FIGS. 1 to 6 can be used in combination with an insertion tool for a closure device. Examples of suitable closure devices are described in US Published Patent Application Nos. 2006/0173492 (Aug. 3, 2006), 2004/0204741 (Oct. 14, 2004) and 2002/0173820 (Nov. 21, 2002). The entire contents of these three publications are incorporated herein by reference for the devices and methods discussed therein.

As has been indicated above, the soft gasket material, which according to the embodiments described herein, functions as a retainer for an introducer adapter should not be regarded as an ordinary seal. For example, to function properly a retainer of the present invention should be rather long, typically between 5 mm and 50 mm long, and have a modulus of elasticity (Young's modulus) that is not too high. A soft gasket material could, for example, have a Young's modulus between 1 MPa and 100 MPa and more preferably between 5 MPa and 50 MPa. At the same time a soft gasket or elastic material should not be too hard, it could, for example, be characterized by a hardness, given in Shore hardness, ranging from 15 OO to 100 A, and more preferably from 10 A to 50 A.

Although the present invention has been described with reference to specific embodiments, also shown in the appended drawings, it will be apparent to those skilled in the art that many variations and modifications can be done within the scope of the invention as described in the specification and defined with reference to the claims below.

What is claimed is:

1. An adapter for use in connecting to a first percutaneous introducer, the adapter comprising:
   a proximal portion;
   a distal portion attached to the proximal portion, the distal portion having an outer circumferential surface; and a retainer formed of a soft elastic material,
wherein the retainer is arranged externally around the distal portion, and has an axial length that is greater than an inner diameter of the retainer,
wherein a diameter of the distal portion is smaller than a diameter of the proximal portion,
wherein at least a part of an inner circumferential surface of the retainer is attached to the outer circumferential surface of the distal portion such that said part is immovable relative to the distal portion during use of the adapter,
wherein the inner circumferential surface of the retainer directly contacts the outer circumferential surface of the distal portion over a substantial portion of the retainer, and
wherein, at a distal end of the distal portion, the outer circumferential surface of the distal portion is not covered by the retainer.

2. The adapter according to claim 1, wherein the distal end of the distal portion comprises a taper that is not covered by the soft elastic material.

3. The adapter according to claim 1, wherein the distal portion is reduced in diameter compared with a diameter of the proximal portion of the adapter and an axial length of the distal portion is at least 1.5 times the diameter of the distal portion.

4. The adapter according to claim 1, wherein the distal portion is reduced in diameter compared with a diameter of the proximal portion of the adapter and an axial length of the distal portion is at least 2 times the diameter of the distal portion.

5. The adapter according to claim 1, wherein the distal portion is reduced in diameter compared with a diameter of the proximal portion of the adapter and an axial length of the distal portion is at least 3 times the diameter of the distal portion.

6. The adapter according to claim 1, wherein the axial length of the retainer is at least 1.5 times the inner diameter of the retainer.

7. The adapter according to claim 1, wherein the axial length of the retainer is at least 2 times the inner diameter of the retainer.

8. The adapter according to claim 1, wherein the axial length of the retainer is at least 3 times the inner diameter of the retainer.

9. The adapter according to claim 1, wherein the retainer is tubular-shaped and has a wall thickness along at least most of its axial length of at least 0.5 mm.

10. The adapter according to claim 1, wherein the retainer is tubular-shaped and has a wall thickness along at least most of its axial length of at least 1.0 mm.

11. The adapter according to claim 1, wherein the retainer is tubular-shaped and has a wall thickness along at least most of its axial length of at least 2.0 mm.

12. The adapter according to claim 1, wherein the retainer is secured to the distal portion at a distal end of the retainer and the retainer is not secured to the distal portion at a proximal end of the retainer.

13. The adapter according to claim 1, wherein an inner surface of the retainer is cylindrically-shaped.

14. The adapter according to claim 13, wherein an outer surface of the retainer is cylindrically-shaped.

15. The adapter according to claim 13, wherein an outer surface of the retainer is tapered along substantially its entire axial length.

16. The adapter according to claim 13, wherein an outer surface of the retainer has a large diameter in a middle portion of the retainer and narrows in diameter towards proximal and distal ends of the retainer.

17. The adapter according to claim 13, wherein an outer surface of the retainer is saw-tooth shaped.

18. The adapter according to claim 1, wherein the distal portion comprises a stem and a head distal to the stem, and wherein an outer diameter of the head exceeds an outer diameter of the stem.

19. The adapter according to claim 1, wherein the adapter further comprises a lug-and-notch arrangement to secure the retainer to the distal portion.

20. The adapter according to claim 18, wherein an outer surface of the stem widens in a distal direction and an inner surface of the retainer has a shape matching the outer surface of the stem.

21. The adapter according to claim 1, wherein the distal portion has a portion that widens in a distal direction.

22. The adapter according to claim 1, wherein the retainer includes a first external circumference at a distal end of the retainer and a second external circumference at a middle portion of the retainer, and wherein the retainer is configured to have the first external circumference be smaller than the second external circumference when the retainer is not deformed by compression caused by contact.

23. The adapter according to claim 1, wherein the retainer includes a first external surface at a distal end of the retainer, wherein the distal portion comprises a second external surface, and wherein the first and second external surfaces align into one continuous tapered surface.

24. The adapter according to claim 1, wherein the retainer is configured to be deformed by being compressed by squeezing contact with a rim of an aperture of an introducer sheath such that the adapter is securely attached to the introducer sheath.

25. The adapter according to claim 1, wherein the adapter is configured to be connected to a distal part of an insertion tool.

26. The adapter according to claim 25, wherein the adapter is formed with the insertion tool so as to form one integral piece.

27. The adapter according to claim 25, wherein the adapter is configured to be releasably attached to the insertion tool.

28. The adapter according to claim 25, wherein the insertion tool comprises a closure device configured to close a puncture hole in a blood vessel.

29. A system of connecting to a percutaneous introducer, comprising:
an insertion tool;
an adapter according to claim 1; and
an introducer sheath having a hub at a proximal end portion, wherein the hub includes an aperture in which the adapter is inserted.

30. The system of claim 29, wherein the insertion tool and the adapter are molded into one piece.

31. The system of claim 29, wherein the adapter is releasably attachable to the insertion tool.

32. The system of claim 29, wherein the retainer has been deformed by being compressed by squeezing contact with a rim of the aperture such that the adapter is securely attached to the hub.

33. The system of claim 29, wherein the retainer has been deformed by being compressed by squeezing contact with a rim of the aperture such that movement of the adapter out from the aperture is inhibited.

34. The system of claim 29, wherein the insertion tool comprises a closure device configured to close a puncture hole in a blood vessel.

35. A system comprising:
- an adapter comprising:
  - a proximal portion;
  - a distal portion attached to the proximal portion, the distal portion having an outer circumferential surface, and
  - a retainer formed of a soft elastic material,
  - wherein the retainer is arranged externally around the distal portion, and has an axial length that is greater than an inner diameter of the retainer,
  - wherein an inner circumferential surface of the retainer directly contacts the outer circumferential surface of the distal portion over a substantial portion of the retainer, and
  - wherein, at a distal end of the distal portion, the outer circumferential surface of the distal portion is not covered by the retainer; and
- an introducer sheath having a hub at a proximal end portion, wherein the hub includes an aperture in which the adapter is insertable such that the retainer is compressed by the hub.

36. The system of claim 35, wherein an insertion tool and the adapter are molded into one piece.

37. The system of claim 35, wherein the adapter is releasably attachable to an insertion tool.

38. The system of claim 35, wherein the retainer has been deformed by being compressed by squeezing contact with a rim of the aperture such that the adapter is securely attached to the hub.

39. The system of claim 35, wherein the retainer has been deformed by being compressed by squeezing contact with a rim of the aperture such that movement of the adapter out from the aperture is inhibited.

40. The system of claim 35, wherein the system comprises a closure device configured to close a puncture hole in a blood vessel.

* * * * *